US008634082B2

(12) United States Patent
Jiang et al.

(10) Patent No.: US 8,634,082 B2
(45) Date of Patent: Jan. 21, 2014

(54) PULSED LASERS IN FREQUENCY DOMAIN DIFFUSE OPTICAL TOMOGRAPHY AND SPECTROSCOPY

(75) Inventors: Shudong Jiang, Hanover, NH (US); Brian William Pogue, Hanover, NH (US); Jia Wang, Rochester, MN (US); Keith D. Paulsen, Hanover, NH (US)

(73) Assignee: The Trustess of Dartmouth College, Hanover, NH (US)

( * ) Notice: Subject to any disclaimer, the term of this patent is extended or adjusted under 35 U.S.C. 154(b) by 836 days.

(21) Appl. No.: 12/665,518

(22) PCT Filed: Jun. 20, 2008

(86) PCT No.: PCT/US2008/067741
§ 371 (c)(1),
(2), (4) Date: Jun. 21, 2010

(87) PCT Pub. No.: WO2008/157790
PCT Pub. Date: Dec. 24, 2008

(65) Prior Publication Data
US 2010/0265493 A1    Oct. 21, 2010

Related U.S. Application Data

(60) Provisional application No. 60/945,198, filed on Jun. 20, 2007.

(51) Int. Cl.
*G01B 9/02* (2006.01)
(52) U.S. Cl.
USPC .......................................... 356/484

(58) Field of Classification Search
USPC ............................................ 356/484
See application file for complete search history.

(56) References Cited

U.S. PATENT DOCUMENTS

2009/0257464 A1* 10/2009 Dantus et al. .................. 372/25

FOREIGN PATENT DOCUMENTS

| CN | 1844732 A | 10/2006 |
|---|---|---|
| WO | 2006077106 A | 7/2006 |
| WO | 2007044821 A | 4/2007 |

OTHER PUBLICATIONS

Wang et al. Optics Letters, vol. 28, Issue 3, pp. 182-184 (2003).*
Pifferi, A., et al.; "Optical Biopsy of Bone Tissue: A Step Toward the Diagnosis of Bone Pathologies;" Journal of Biomedical Optics SPIE, USA; vol. 9, No. 3, May 2004, pp. 474-480.
International Search Report and Written Opinion in related PCT/US2008/067741 dated Oct. 22, 2009, 20 pages.

* cited by examiner

*Primary Examiner* — Tarifur Chowdhury
*Assistant Examiner* — Sunghee Y Gray
(74) *Attorney, Agent, or Firm* — Lathrop & Gage LLP

(57) ABSTRACT

A diffuse optical tomography system incorporating a mode-locked, tunable laser produces pulsed light that may be used to interrogate tissue with high spatial and spectral resolution. The detection signal may be heterodyne shifted to lower frequencies to allow easy and accurate measurement of phase and amplitude. Embodiments incorporating wavelength-swept, tunable, lasers and embodiments using broadband photonic fiber lasers with spectrally-sensitive detectors are described.

5 Claims, 3 Drawing Sheets

PULSED LASERS IN FREQUENCY DOMAIN DIFFUSE OPTICAL TOMOGRAPHY AND SPECTROSCOPY

RELATED APPLICATIONS

This application claims the benefit of U.S. Provisional Patent Application Ser. No. 60/945,198, filed Jun. 20, 2007, the disclosure of which is incorporated herein by reference.

U.S. GOVERNMENT RIGHTS

This invention was made with Government support under grants NIH RO1 N539471, U54 CA105480 and K25CA106863 awarded by the National Institutes of Health. The U.S. Government has certain rights in this invention.

BACKGROUND

Diffuse Optical Tomography (DOT) is a technique wherein tissue is illuminated at multiple source points on a tissue surface with light having wavelengths ranging from visible light to near infrared (NIR). Light transmitted through the tissue from each source point is detected at multiple reception points on the tissue surface, and a measure of attenuation (absorption and scattering) along paths from each source point to each reception point is obtained to estimate the chromophore, fluorophore or scatterer concentrations.

Modeling of the absorption and scattering creates potentially high contrast images containing functional tissue information. For example, the heme group of myoglobin and/or hemoglobin absorbs visible and near infrared light, and the spectral characteristics of the absorption vary noticeably with the degree of oxygenation. Therefore, high contrast may be obtained between portions of tissue containing high concentrations of heme (such as blood and muscle) and portions of tissue containing low concentrations of heme (such as fat), and between highly oxygenated and poorly oxygenated or infarcted tissues. In particular, the high vascularity of tumors often provides them a significant hemoglobin content and a potentially high intrinsic optical contrast between the tumor and normal tissue.

Scattering and absorption can, however, be difficult to distinguish when DOT is performed with monochromatic, continuous-wave radiation because the transmitted or reflected light is diffuse and intensity is generally low. Distinctions between background noise, scattering, and absorption, may be improved by the use of modulated illumination and AC-coupled amplification at multiple wavelengths. To produce the modulated light, most existing DOT systems use either amplitude modulated laser diodes or light-emitting diodes (LEDs) that operate at different wavelengths. However, there are a limited number of available wavelengths of laser diodes or LEDs that generate enough power to provide a high signal-to noise ratio and lase at wavelengths suitable for probing biological chromophores.

Tunable titanium-sapphire lasers have been used for studies of optical absorption in mammalian tissues. For example, "Optical biopsy of bone tissue: a step toward the diagnosis of bone pathologies", Pifferi et al., Journal of Biomedical Optics 9(3), 474-480 (May/June 2004) describes using a mode-locked, tunable from 700 to 1000 nanometers wavelength, titanium-saphire (Ti:Saphire) pulsed laser and a dye laser tunable from 650 to 695 nanometers with a single 1 mm optical fiber for delivering light to a single point on a heel and a single 5 mm optical fiber bundle for receiving light from the heel and delivering the light to a time-resolved photomultiplier-tube photodetector.

Time resolved transmittance spectroscopy has also been used in optical spectrometry of soft tissues. "Absorption of collagen: effects on the estimate of breast composition and related diagnostic implications", Taroni et al., Journal of Biomedical Optics 12(1), 014021 1-4 January/February 2007, describes absorption spectrometry of the breast. The apparatus of Taroni is probably similar to that used by co-author Pifferi. The apparatus of Taroni provides spectra of, for example, absorption along a single path between two points through the tissue. The apparatus of Taorni does not provide images resolving inclusions within the tissue. Taroni acknowledges that spectroscopy may have a role in imaging but does not discuss how this might be done and does not discuss alternative light detection approaches.

SUMMARY

In one embodiment, a tomography system includes: a mode-locked, tunable laser for generating pulsed light of a predeterminable wavelength, the pulsed light characterized by a first pulse repetition frequency; an apparatus for applying the pulsed light to tissue at a source position; apparatus for collecting light from the tissue at a plurality of detector positions; an apparatus for transducing the collected light into a plurality of detection signals; an apparatus for supplying a reference signal characterized by the first pulse repetition frequency; and an image construction apparatus for receiving the plurality of detection signals and the reference signal and constructing a tomographic image of the tissue based at least in part on a comparison of the detection signals and the reference signal.

In one embodiment, a method for generating tomographic images of tissue includes: generating pulsed light from a pulsed, tunable laser, the pulsed light characterized by a first pulse repetition frequency; applying the pulsed light to a source position on the tissue; receiving transmitted light at a plurality of detector positions; transducing the transmitted light into electrical signals; generating a reference signal characterized by the first pulse repetition frequency; and constructing the tomographic image of the tissue based at least in part on a comparison of the electrical signals and the reference signal.

In one embodiment, a tomography system includes: a mode-locked, broadband tunable laser for generating pulsed light, the pulsed light characterized by a first pulse repetition frequency; an apparatus for applying the pulsed light to tissue at a source position; apparatus for collecting light from the tissue at a plurality of detector positions; a spectrally-sensitive apparatus for transducing the collected light into a plurality of detection signals embodying wavelength information; and an image construction apparatus for receiving the plurality of detection signals and the reference signal and constructing a tomographic image of the tissue.

DETAILED DESCRIPTION OF THE EMBODIMENTS

In the following description, the term light is used to represent electromagnetic radiation from the near infrared part of the spectrum into the visible range. The term light should therefore not be taken as a limitation to visible parts of the electromagnetic spectrum.

As discussed in more detail below, the disclosed systems and methods utilize a pulsed, tunable laser for near infrared diffuse optical tomography. The pulsed, tunable laser may for example be a mode-locked, pulsed-output, tunable laser driven by a continuous-wave pumping laser. One example of a pulsed-output, tunable laser is a Kerr-lens self-mode-locked (KLM) titanium sapphire (Ti:S) laser, which provides continuous wavelength tuning in a range from about 650-1100 nm and a power output of about 0.5 to 3 Watts in ultrafast pulses. Light pulses from a mode-locked Ti:S laser typically have pulse durations of between about five femtoseconds and a few picoseconds, with a pulse repetition frequency of between 70-90 MHz. The high power output of such lasers helps produce a high signal-to-noise ratio that improves spatial resolution relative to traditional laser diode systems. In addition, the wide tunable range allows data collection over a significant portion of the near-infrared wavelength range and reduces crosstalk between important chromophores, thereby improving spectral resolution.

Figure 1:
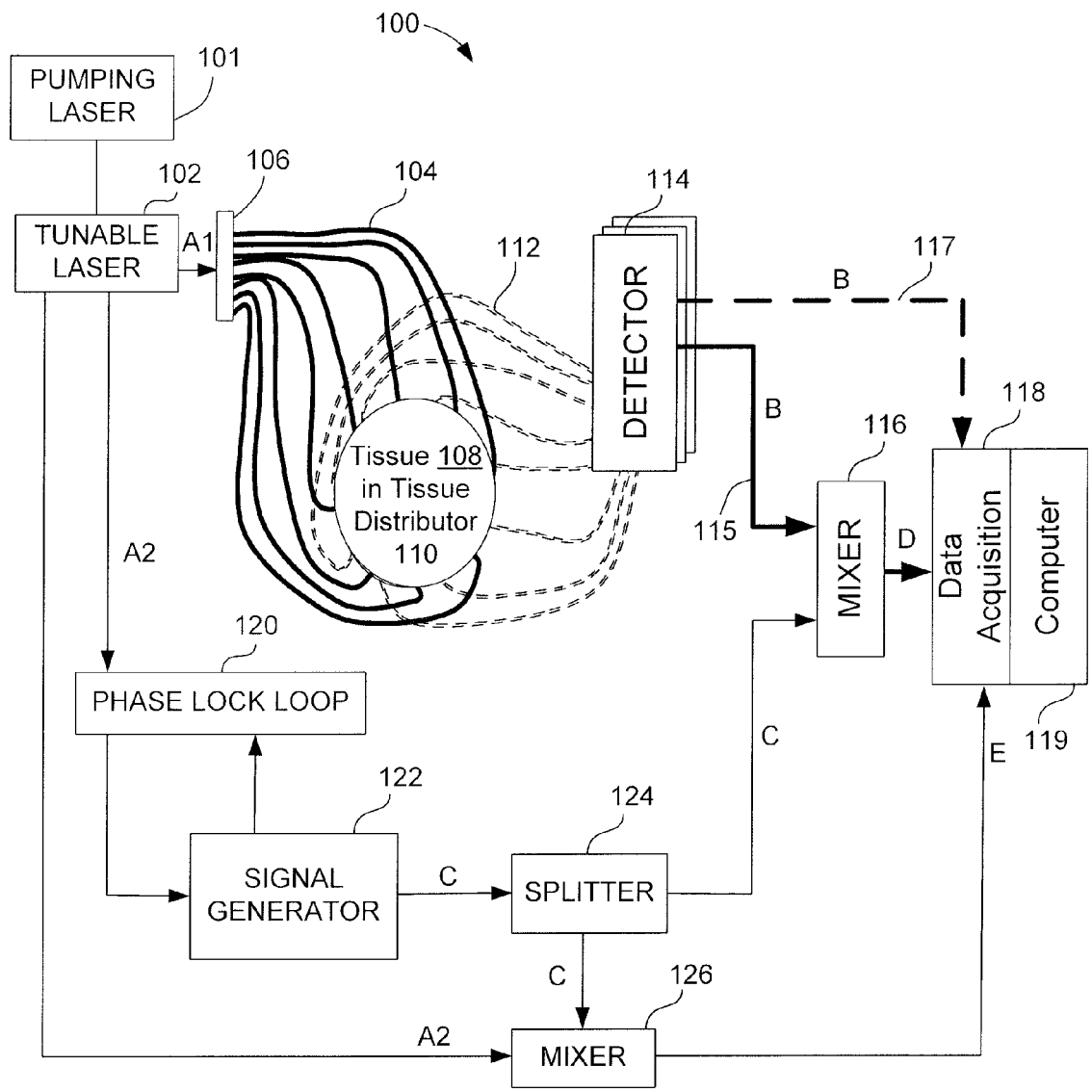
FIG. 1 is a block diagram showing one exemplary optical imaging system embodiment using pulsed lasers for frequency domain diffuse optical tomography.

FIG. 1 shows one exemplary optical imaging system 100. System 100 includes a pumping laser 101 which may be a continuous-wave high-power laser diode, an argon ion laser or a frequency-doubled neodymium yttrium orthovanadate ($Nd:YVO_4$) laser, for pumping a mode-locked, tunable laser 102.

Light, A1, emitted by laser 102 enters an optical transmit fiber 104 by way of a selector 106. Selector 106 may be a rotating disk mechanically adjusted to sequentially select new source positions (i.e., transmit fibers 104). Tissue 108, which may be disposed in a tissue distributor 110, is exposed to light A1 from one of transmit fibers 104. Tissue 108 may contain inclusions, not shown, the inclusions may incorporate chromophores having absorption and scattering properties differing from other constituents of tissue 108.

Exemplary tissue distributors 110 are described, for example, in T. O. McBride; B. W. Pogue; E. D. Gerety; S. B. Poplack; U. L. Österberg; K. D. Paulsen, "Spectroscopic diffuse optical tomography for the quantitative assessment of hemoglobin concentration and oxygen saturation in breast tissue", Applied Optics, 38(25), 5480-5490, 1 Sep. 1999 and B. W. Pogue; M. Testorf; T. McBride; U. Österberg; K. Paulsen, "Instrumentation and design of a frequency-domain diffuse optical tomography imager for breast cancer detection", Opt. Exp. 1, 391-403 (1997). A tissue model, or phantom, may be used in place of tissue 108 during development and calibration.

An optode is a device that serves as the optical equivalent of an electrode—it serves to couple light from a transmit fiber 104 into tissue 108, or from tissue 108 to receive fiber 112. Distributor 110 incorporates multiple receive optodes at different positions around tissue 108, as well as multiple transmit optodes at multiple positions around tissue 108.

Light exiting tissue 108 is collected by receive optodes of distributor 110, each receive optode couples this light into one of several receive fibers 112. Each receive fiber 112 couples light to a detector 114. Receive fibers 112 may be multiplexed into a single detector 114, or multiple detectors may be provided. Detector(s) 114 may include one or more of photomultiplier tubes (PMTs), avalanche photodiode modules, charge coupled devices (CCDs) or other known detectors. Each detector 114 transduces received light from receive fiber 112 into a modulated electrical signal, B, that is sent to a data acquisition device 118 of a computer 119, via a communication path 117, when only intensity is being measured. Where multiple detectors 114 are used, communication path 117 may represent multiple signal pathways.

However, in order to allow for amplification and precise measurement of a delay in the detected light resulting from migration of the light through tissue 108, detected signals B, which have the pulse repetition frequency of laser 102 (typically between 70-90 MHz), are heterodyned to a frequency that is sampleable by a clock of high resolution data acquisition device 118, typically in the range from 5 Hz to 200 KHz. Data acquisition device 118 feeds information to computer 119.

Signals B may be measured either in sequence or in parallel by data acquisition device 118. Sampling in sequence may be facilitated by a multiplexer within data acquisition device 118.

Heterodyning of electrical signals B is accomplished by a mixer(s) 116, driven by a local signal generator 122. Mixer(s) 116 combine signal B, received via communication path 115, with a secondary signal, C, received from a splitter 124. The difference between signal B and signal C produces detected mixed signal D characterized by a beat frequency that may be sampled by data acquisition device 118. For example, when signal B has a pulse repetition frequency of 80 MHz and signal C has a frequency of 79.998 MHz, the difference between signal B and signal C yields signal D having a beat frequency of 2 KHz, which is readily amplifiable with AC-coupled amplifiers and measurable by data acquisition device 118.

Reference signal C is generated by a signal generator 122, and, in order to stabilize the beat frequency, is phase locked (synchronized) to a predetermined ratio of the pulse repetition frequency of laser 102 by a phase locked loop 120. Phase locked loop 120 may be an integrated circuit. A portion of reference signal C is also sent, via splitter 124, to a second mixer 126 where it is mixed with signal A2, which is a clock signal having the same pulse repetition frequency as light A1; this creates a reference signal E that may be sampled by data acquisition device 118. In the absence of reference signal C, signal A2 may be transmitted as a non-heterodyned signal to data acquisition device 118.

Detected mixed signal D and reference signal E are acquired by data acquisition device 118 and read by computer 119, which measures the amplitude and phase of these signals to determine an attenuation of light A1 due to transmission through tissue 108.

Computer 119 may contain a processor, executing image construction software known in the art, and a display. Images may also be recorded to a memory of computer 119 for later study.

In one example, tunable laser 102 may be scanned across a wavelength range, e.g., from 690 nm to 1000 nm, in set increments, e.g., 5 nm, thereby providing for data acquisition at sixty-three wavelengths. In another example of operation, laser 102 is set to lase at a particular wavelength (e.g., under control of software instructions executed by computer 119), and light is distributed through each one of transmit fibers 104 in sequence, e.g. fiber 104(1) . . . fiber 104(n). In this way, the present systems and methods utilize the pulse repetition frequency of laser 102 to mimic the intensity modulation of laser diodes in a traditional DOT system. Upon completion of a first cycle (i.e., after transmit fiber 104(n) has been illuminated), laser 102 is tuned to a new wavelength (e.g., $\lambda_1$+5 nm), and the process of illuminating each transmit fiber 104 is repeated.

In an embodiment wherein laser 102 is set to lase at particular wavelengths, at least three wavelengths in the range from 650 to 1100 nanometers are used to permit distinguishing oxygenated from non-oxygenated heme groups.

Changes may be made to system 100 without departing from the scope hereof. For example, an optical fiber that acts as a transmit fiber 104 in one instance may become a receive fiber 112 when a new transmit fiber 104 is selected by selector 106. In another example, mixer 116 may form part of a photomultiplier tube.

The heterodyne technique for amplifying and detecting transmitted light, using phase lock loop 120 and mixer 116, permits high sensitivity, noise immunity, and rapid data acquisition. This high sensitivity and rapid data acquisition in turn permits use of the system to observe dynamic changes in chromophores, such as may occur during neural or muscle activity. Since noise photons, including photons originating from other sources of illumination such as room lighting, those originating from fluorescence in tissue 108, and infrared photons radiated by the tissue 108, arrive with random timing with respect to the laser pulses, these photons tend to cancel each other and are ignored by the system. The system therefore has improved noise rejection compared to single-photon-counting systems such as that of Pifferi and Taroni.

Figure 2:
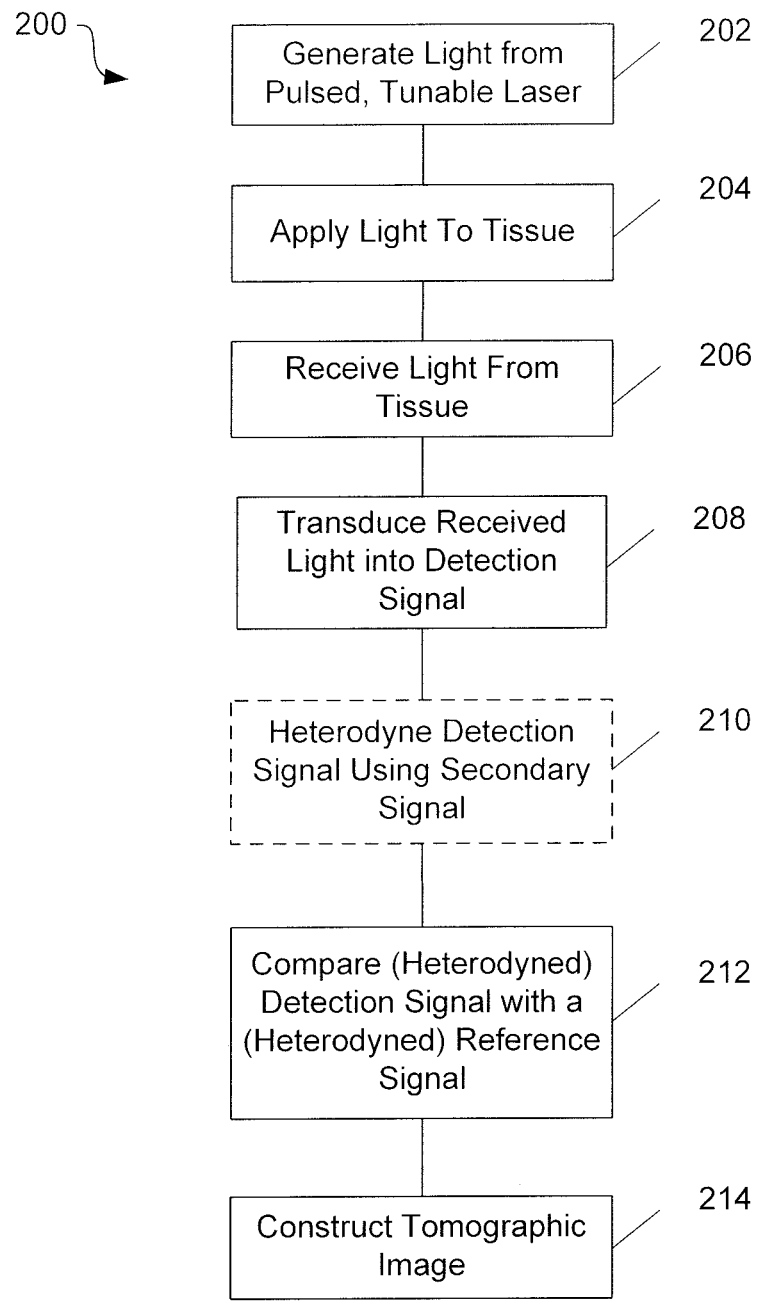
FIG. 2 is a flowchart illustrating one process for generating an optical image using the system of FIG. 1.

FIG. 2 shows a flowchart illustrating one process 200 for generating an optical image using system 100 of FIG. 1. In step 202, a specific wavelength of light (e.g., 690 nm) is generated by tunable laser 102. In an example of step 202, a processor of computer 119 may execute software containing instructions for an illumination wavelength, pulse repetition frequency, etc. of tunable laser 102. In order to implement these instructions, computer 119 may control some or all of the components of system 100. In step 204, light is applied to tissue 108 through a transmit fiber 104. After the light migrates through tissue 108, it is received by receive fibers 112 at multiple reception points on tissue 108 in step 206. In step 208, the received light is transduced into a detection signal. In an example of step 208, detector 114 converts light received through receive fibers 112 into electrical signals B. Step 210 is optional. In step 210, the detection signal is heterodyned to a lower frequency by mixing with a secondary signal to provide a resultant signal (e.g., signal D). In step 212, the detection signal, having either a heterodyned or non-heterodyned pulse repetition frequency, is compared to a reference signal. If the detection signal is heterodyned, the reference signal is also heterodyned to the same pulse repetition frequency. If the detection signal is non-heterodyned, the reference signal is also non-heterodyned. In step 214, a tomographic image is constructed by a processor of computer 119 based at least in part on the comparative data.

Figure 3:
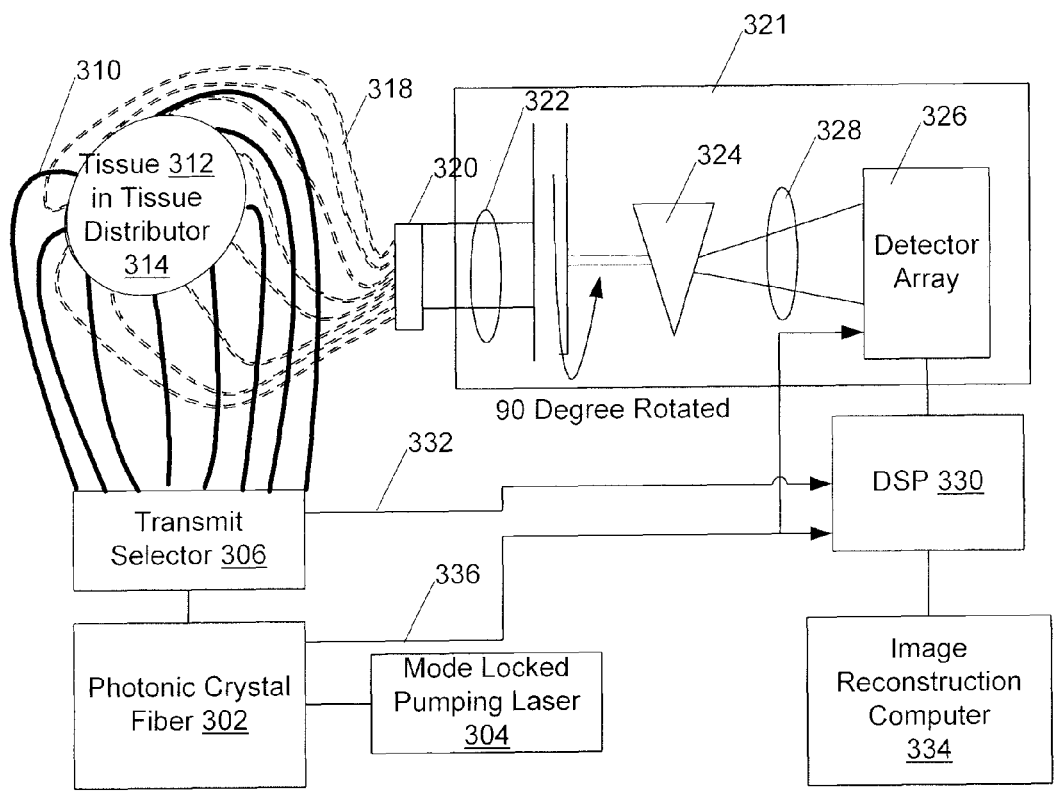
FIG. 3 is a block diagram showing an alternative embodiment having a photonic crystal fiber for transforming laser pulses into broadband light pulses and an array detector.

In another embodiment, as illustrated in FIG. 3, a photonic crystal fiber 302 is used to generate a pulsed broadband or "white" light source. Photonic crystal fibers are microstructured light guides that, in some cases, when stimulated by laser pulses, can act as broadband lasers. For example, when pumped by mode-locked pulsed laser 304 crystal fiber 302 generates a pulse of light having energy essentially evenly distributed from the infrared to green wavelengths. The light from crystal fiber 302 is distributed by transmit selector 306 into transmit optical fibers 308 one at a time in sequence.

Light from each transmit fiber 310 is provided to tissue 312 through a optode for each transmit fiber in tissue distributor 314.

Light is collected by receive optodes of tissue distributor 314 and transmitted by receive optical fibers 318 to a slit 320. At slit 320 the receive optical fibers are placed adjacent to each other such that light transmitted by all fibers 318 illuminates a short line at the slit 320, and that light received from each fiber 318 illuminates a particular nonoverlapping portion of the short line; this line is imaged by a spectrographic imager 321.

Within spectrographic imager 321, light from slit 320 is focused by lenses 322 into a dispersive device 324 oriented such that light of the line is spread by wavelength into a rectangle on photodetector array 326. Dispersive device 324 may be a prism or may be a diffraction grating as known in the art of spectroscopy. Light from each fiber 318 is dispersed by wavelength across a row of pixels on photodetector 326 that does not overlap the rows of pixels illuminated by other fibers 318. Light at each pixel of detector 326 is light of a specific wavelength received from a particular fiber.

Additional lenses 328 may be present in the optical path as necessary to properly focus spectra from receive fibers 318 onto photodetector array 326.

For convenience in illustration, dispersive device 324 and photodetector array 326 are rotated by ninety degrees with respect to slit 320 as viewed in FIG. 3.

Signals representative of light received by each pixel of photodetector 326 are passed to digital signal processor 330. Digital signal processor also receives a synchronization signal 332 from transmit selector 306 and determines a spectra of light transmission along each path through tissue 312 from each transmit optode of distributor 314 to each receive optode of distributor 314. The spectra of light transmission along each path are used by image reconstruction 334 to produce a tomographic image of inclusions within tissue 312.

In an embodiment, photodetector 326 is electronically gated by a reference signal 336. Detected photons arriving during and immediately after light pulses emitted by photonic crystal fiber laser 302 are accumulated and averaged to produce a "lighted" signal. Detected photons, such as noise photons, arriving at other times are accumulated and averaged to produce a "dark" signal. The spectra of light transmission along each path is determined in part by subtracting the dark signal from the light signal.

Combined broadband spectroscopy and frequency domain spectroscopy may be useful in disease or physiological imaging where the spectral content of the signal can be acquired rapidly.

In an alternative embodiment particularly suited to rapid data acquisition, several pumping lasers 304 and photonic crystal fiber lasers 302 are used. In this embodiment, transmit selector 306 may act as a multipole switch, permitting several transmit fibers 310 to be coupled to different crystal fiber lasers 302 simultaneously. In this embodiment, crystal fiber lasers 302 are sequenced electronically and at a high rate such that paths through tissue 312 from different transmit fibers to receive fibers 318 can be distinguished. Similarly, if a crystal fiber laser 302 is provided for each transmit fiber 310, transmit selector 306 may be deleted.

Figure 4:
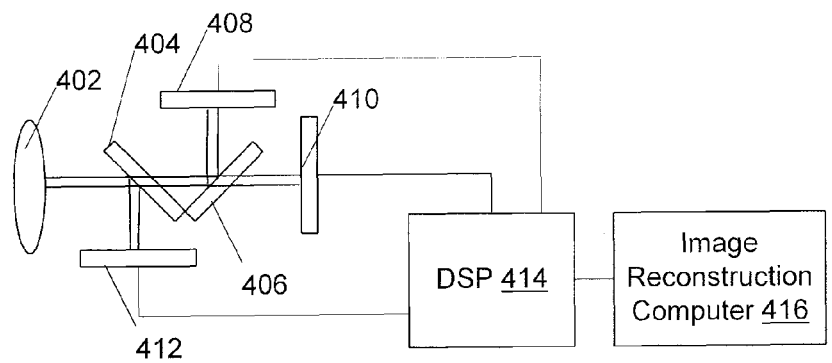
FIG. 4 is a block diagram of an alternative embodiment having a broadband illumination and using dichroic filters with multiple photodetectors.

In an alternative embodiment, illustrated in FIG. 4 with reference to FIG. 3, a pumping laser 304, photonic crystal fiber laser 302, transmit fibers 310, optodes and tissue distributor 314, receive fibers 318, and slit 320 are provided similar to the embodiment of FIG. 3. Light from slit 320 is transmitted through a lens system 402 and through a series of dichroic filters 404, 406 to separate the light into separate beams corresponding to differing wavelengths of light received from receive fibers 318. Each of these separate beams is received by a photodetector 408, 410, 412 of a type suitable for receiving light of wavelengths of that beam. Photodetectors 408, 410, 412 may be linear array photodetectors such that each pixel elements of the photodetectors 408, 410, 412 receive light corresponding to particular fibers of receive fibers 318. Signals from photodetectors 408, 410, 412 are processed by digital signal processor 414 and passed to an image reconstruction computer 416.

Specific applications in which the present system may be used include: assessment of disease or response to therapy; monitoring uptake or retention of drugs or dyes, which are optically absorbing or scattering; detection of epidural and subdural hematomas; and imaging of tumors. For example, the disclosed systems and methods may be used to generate images useful in the diagnosis and/or treatment of breast cancer, brain cancer, prostate cancer, aneurisms, hematomas, tumors, cysts, heart disease, renal artery stenosis, peripheral vascular disease and vulnerable plaques in arteries.

The changes described above, and others, may be made in the systems and methods described herein without departing from the scope hereof. It should thus be noted that the matter contained in the above description or shown in the accompanying drawings should be interpreted as illustrative and not in a limiting sense. The following claims are intended to cover all generic and specific features described herein, as well as all statements of the scope of the present systems and methods, which, as a matter of language, might be said to fall there between.

What is claimed is:

1. A tomography system, comprising:
   a pulsed, tunable laser for generating pulsed light of a predeterminable wavelength and a first pulse repetition frequency,
   wherein the pulsed, tunable laser generates a reference signal characterized by the first pulse repetition frequency;
   a transmit fiber coupled to apply the pulsed light to tissue at a source position;
   a plurality of receive fibers each coupled to receive light from the tissue at a receive optode position, wherein there are a plurality of receive optode positions;
   detectors for transducing the collected light into a plurality of detection signals,
   a computer for receiving the plurality of detection signals and the reference signal and constructing a tomographic image of the tissue;
   a signal generator for generating a secondary signal characterized by a second pulse repetition frequency;
   a first mixer for mixing the secondary signal with the detection signals to form first heterodyned signals characterized by a third frequency; and
   a second mixer for mixing the secondary signal with the reference signal to form a second heterodyned signal characterized by the third frequency;
   wherein the computer is configured to receive the first and second heterodyned signals and construct the tomographic image of the tissue based at least in part on a comparison of the first and second heterodyned signals, and configured to use the reference signal to control reception of the detection signals.

2. The tomography system of claim 1, wherein the first and second heterodyned signals have frequencies in a range of 5 Hz to 200 KHz.

3. A method for generating tomographic images of tissue, comprising:
   (a) generating pulsed light from a pulsed, tunable laser, the pulsed light characterized by a wavelength and a first pulse repetition frequency;
   (b) applying the pulsed light to a source position on the tissue;
   (c) receiving light at a plurality of detector positions on the tissue;
   (d) transducing the received light into electrical signals;
   (e) generating a reference signal characterized by the first pulse repetition frequency; and
   (f) constructing the tomographic image of the tissue based at least in part on a comparison of the electrical signals and the reference signal;
   (g) generating a secondary signal characterized by a second pulse repetition frequency;
   (h) mixing the electrical signals with the secondary signal to produce first heterodyned signals characterized by a third frequency;
   (i) mixing the reference signal with the secondary signal to produce a second heterodyned signal characterized by the third frequency; and
   (j) constructing the tomographic image of the tissue based at least in part on a comparison of the first and second heterodyned signals.

4. The method of claim 3, further comprising altering the wavelength of the pulsed light and repeating steps (a)-(j).

5. The method of claim 4, wherein the wavelength of pulsed light is set to at least three wavelengths at least five nanometers apart in the range of 650 and 1100 nanometers.

* * * * *